United States Patent
Minagawa

(10) Patent No.: US 10,413,638 B2
(45) Date of Patent: Sep. 17, 2019

(54) SURFACE-MODIFIED RUBBER OR SURFACE-MODIFIED THERMOPLASTIC ELASTOMER AND METHOD FOR MODIFYING SURFACE OF RUBBER OR THERMOPLASTIC ELASTOMER

(71) Applicant: SUMITOMO RUBBER INDUSTRIES, LTD., Kobe-shi, Hyogo (JP)

(72) Inventor: Yasuhisa Minagawa, Kobe (JP)

(73) Assignee: SUMITOMO RUBBER INDUSTRIES, LTD., Kobe-shi, Hyogo (JP)

(*) Notice: Subject to any disclaimer, the term of this patent is extended or adjusted under 35 U.S.C. 154(b) by 114 days.

(21) Appl. No.: 14/953,089

(22) Filed: Nov. 27, 2015

(65) Prior Publication Data
US 2016/0184486 A1 Jun. 30, 2016

(30) Foreign Application Priority Data
Dec. 26, 2014 (JP) .................... 2014-264609

(51) Int. Cl.
| | | |
|---|---|---|
| A61L 31/04 | (2006.01) | |
| A61L 29/04 | (2006.01) | |
| A61L 29/06 | (2006.01) | |
| A61L 29/08 | (2006.01) | |
| A61L 31/06 | (2006.01) | |
| A61L 31/10 | (2006.01) | |
| A61L 31/14 | (2006.01) | |
| C08F 253/00 | (2006.01) | |
| C08F 283/00 | (2006.01) | |
| C08F 283/04 | (2006.01) | |

(52) U.S. Cl.
CPC .......... *A61L 31/048* (2013.01); *A61L 29/042* (2013.01); *A61L 29/06* (2013.01); *A61L 29/085* (2013.01); *A61L 31/049* (2013.01); *A61L 31/06* (2013.01); *A61L 31/10* (2013.01); *A61L 31/14* (2013.01); *C08F 253/00* (2013.01); *C08F 283/006* (2013.01); *C08F 283/04* (2013.01); *A61L 2400/10* (2013.01); *A61L 2420/02* (2013.01); *A61L 2420/06* (2013.01); *A61L 2420/08* (2013.01)

(58) Field of Classification Search
None
See application file for complete search history.

(56) References Cited

U.S. PATENT DOCUMENTS

| | | | | |
|---|---|---|---|---|
| 6,358,557 | B1* | 3/2002 | Wang | ................... A61L 29/085 427/2.24 |
| 2013/0310772 | A1* | 11/2013 | Minagawa | .............. C08C 19/28 604/265 |
| 2015/0284487 | A1 | 10/2015 | Minagawa | |

FOREIGN PATENT DOCUMENTS

| | | |
|---|---|---|
| JP | 50-10387 A | 2/1975 |
| JP | 6-510322 A | 11/1994 |
| JP | 10-298320 A | 11/1998 |
| JP | 11-172027 A | 6/1999 |
| JP | 2003-510378 A | 3/2003 |
| JP | 2011-188908 A | 9/2011 |
| JP | 2011-219520 A | 11/2011 |
| JP | 2013-237802 A | 11/2013 |
| JP | 2014-47296 A | 3/2014 |
| JP | 2014-132059 A | 7/2014 |
| WO | WO 2014/080873 A1 | 5/2014 |

OTHER PUBLICATIONS

Hu et al., "Surface Grafting on Polymer Surface Using Physisorbed Free Radical Initiators," Macromolecules, vol. 38, No. 15, 2005 (published online Jun. 22, 2005), pp. 6592-6597.

* cited by examiner

*Primary Examiner* — Nathan T Leong
(74) *Attorney, Agent, or Firm* — Birch, Stewart, Kolasch & Birch, LLP

(57) ABSTRACT

Provided are surface-modified rubbers or surface-modified thermoplastic elastomers, such as catheters, syringe barrels, tubes of medical instruments, and mudguard fenders, and methods for modifying the surface of rubber or a thermoplastic elastomer, wherein a lubricant layer is firmly bonded to the surface of medical devices such as catheters, syringe barrels, and tubes of medical instruments to impart lubricity to the surface and, further, improve the durability of the lubricant layer on the surface, thereby suppressing deterioration of the sliding properties. Included is a surface-modified rubber or a surface-modified thermoplastic elastomer each having a surface at least partially treated by polymerization of a monomer in the presence of a thermal polymerization initiator.

4 Claims, No Drawings

SURFACE-MODIFIED RUBBER OR SURFACE-MODIFIED THERMOPLASTIC ELASTOMER AND METHOD FOR MODIFYING SURFACE OF RUBBER OR THERMOPLASTIC ELASTOMER

TECHNICAL FIELD

The present invention relates to surface-modified rubbers or surface-modified thermoplastic elastomers, and methods for modifying the surface of rubber or a thermoplastic elastomer.

BACKGROUND ART

Catheters used in the medical field and the like, such as vascular catheters and urethral catheters for urethral catheterization, and the like are inserted into blood vessels, digestive tracts, tracheae, bile ducts, or ureters and used in aqueous solutions such as blood and body fluids. They are thus required to be able to be smoothly inserted without damaging tissues.

In this context, a low friction lubricant is applied to the surface of a catheter, or the surface is coated with a lubricant layer, before use (see Patent Literature 1). However, these techniques have drawbacks in that the surfaces thus treated have insufficient lubricity, and that since the lubricants are not chemically fixed to the surfaces of catheters, they are, for example, separated or peeled during the movement within a vessel or tract, with the result that the lubricity is reduced.

CITATION LIST

Patent Literature

Patent Literature 1: JP 2011-188908 A

SUMMARY OF INVENTION

Technical Problem

The present invention aims to solve the above problems and provide surface-modified rubbers or surface-modified thermoplastic elastomers, such as catheters, syringe barrels, tubes of medical instruments, and mudguard fenders, and methods for modifying the surface of rubber or a thermoplastic elastomer, wherein instead of a resin coating which has drawbacks, such as that lubricity is reduced due to separation, peeling or the like of the coating during the movement within a vessel or tract, a lubricant layer is firmly bonded to the surface of medical devices such as catheters, syringe barrels, and tubes of medical instruments to impart lubricity to the surface and, further, improve the durability of the lubricant layer on the surface, thereby suppressing deterioration of the sliding properties.

Solution to Problem

The present invention encompasses a surface-modified rubber or a surface-modified thermoplastic elastomer each having a surface at least partially treated by polymerization of a monomer in the presence of a thermal polymerization initiator.

The thermal polymerization initiator is preferably present as an adsorbate on the surface.

The surface is preferably further treated, after the polymerization of a monomer in the presence of a thermal polymerization initiator, by polymerization of a monomer at least once in the presence of a thermal polymerization initiator optionally present as an adsorbate on the surface.

The monomer is preferably at least one selected from the group consisting of a hydrophilic monomer, a metal salt-containing hydrophilic monomer, and a halogen-containing hydrophilic monomer.

The surface-modified rubber or surface-modified thermoplastic elastomer preferably includes at least one selected from the group consisting of natural rubber, deproteinized natural rubber, silicone rubber, nylon, and polyurethane.

The present invention also encompasses a medical device, including the surface-modified rubber or surface-modified thermoplastic elastomer.

The medical device is preferably a catheter, a syringe barrel, or a tube of a medical instrument.

The present invention further encompasses a method for modifying a surface of rubber or a thermoplastic elastomer, including the step of growing polymer chains on the surface of rubber or a thermoplastic elastomer by polymerizing a monomer in the presence of a thermal polymerization initiator on the surface of rubber or a thermoplastic elastomer.

The method preferably includes, after the step of growing polymer chains, the step of further polymerizing a monomer at least once in the presence of a thermal polymerization initiator optionally present as an adsorbate on the surface.

Advantageous Effects of Invention

According to the present invention, since the surface of rubber or a thermoplastic elastomer is treated by polymerization of a monomer in the presence of a thermal polymerization initiator, a polymer derived from the monomer is consequently chemically bonded to the rubber or thermoplastic elastomer surface to impart lubricity to the rubber or thermoplastic elastomer surface and, further, improve the durability of the lubricant layer on the surface, thereby suppressing deterioration of the sliding properties of the rubber or thermoplastic elastomer surface.

DESCRIPTION OF EMBODIMENTS

The surface-modified rubbers or surface-modified thermoplastic elastomers of the present invention have a surface at least partially treated by polymerization of a monomer in the presence of a thermal polymerization initiator.

Lubricant layers formed on the surfaces of rubbers or thermoplastic elastomers by conventional surface treatment or coating methods are not chemically bonded to the surfaces and can be easily peeled or removed by a stress such as rubbing by a hand, friction with an object contacting the rubber or thermoplastic elastomer (e.g., the inside of a blood vessel, cells in the body), flows of chemicals or blood, or the like. Thus, they are disadvantageous in terms of maintaining durability and sliding properties. In contrast, in the case of the surface-modified rubbers or surface-modified thermoplastic elastomers of the present invention, the surface treatment consisting of polymerization of a monomer in the presence of a thermal polymerization initiator allows a polymer derived from the monomer to be chemically bonded to the surface of rubber or a thermoplastic elastomer. Therefore, peeling or removal of the lubricant layer on the rubber or thermoplastic elastomer surface due to a stress, friction, liquid flows, or the like can be inhibited, and deterioration of the sliding properties of the rubber or thermoplastic elastomer surface can be suppressed.

The surface-modified rubbers or surface-modified thermoplastic elastomers of the present invention have a surface treated by polymerization of a monomer in the presence of a thermal polymerization initiator, at least at a portion where lubricity is required although the entire surface may be treated as above.

Examples of the thermal polymerization initiator include azo compounds and peroxide compounds. Preferred among these are azo compounds. These thermal polymerization initiators may be used alone or in combinations of two or more.

Examples of azo compounds that can be used as the thermal polymerization initiator include azobisisobutyronitrile (AIBN), 2,2'-azobis[2-(2-imidazolin-2-yl)propane]dihydrochloride, 2,2'-azobis[2-(2-imidazolin-2-yl)propane] disulfate dihydrate, 2,2'-azobis(2-methylpropionamidine) dihydrochloride, 2,2'-azobis[N-(2-carboxyethyl)-2-methylpropionamidine]hydrate, 2,2'-azobis[2-(2-imidazolin-2-yl) propane], 2,2'-azobis(1-imino-1-pyrrolidino-2-methylpropane) dihydrochloride, 2,2'-azobis[2-methyl-N-(2-hydroxyethyl)propionamide], 2,2'-azobis(4-methoxy-2,4-dimethylvaleronitrile), 2,2'-azobis(2,4-dimethylvaleronitrile), dimethyl 2,2'-azobis(2-methylpropionate), 2,2'-azobis(2-methylbutyronitrile), 1,1'-azobis(cyclohexane-1-carbonitrile), 2,2'-azobis[N-(2-propenyl)-2-methylpropionamide], 1,1'-azobis(1-acetoxy-1-phenylethane), dimethyl 2,2'-azobisisobutyrate, and derivatives of these compounds. Among these, suitable are azobisisobutyronitrile and derivatives thereof.

Examples of peroxide compounds that can be used as the thermal polymerization initiator include PERHEXA (registered trademark) V (n-butyl4,4-di(t-butylperoxy)valerate), PERHEXA (registered trademark) C (1,1-di(t-butylperoxy) cyclohexane), PERCUMYL (registered trademark) H (cumene hydroperoxide), PERCUMYL (registered trademark) P (diisopropylbenzene hydroperoxide), PERBUTYL (registered trademark) C (t-butyl cumyl peroxide), PERHEXYL (registered trademark) D (di-t-hexyl peroxide), PEROYL (registered trademark) L (dilauroyl peroxide), PEROYL (registered trademark) NPP (di-n-propyl peroxydicarbonate), PEROYL (registered trademark) SBP (di-sec-butyl peroxydicarbonate), PERCUMYL (registered trademark) ND (cumyl peroxyneodecanoate), PERHEXA (registered trademark) 25O (2,5-dimethyl-2,5-di(2-ethylhexanoylperoxy)hexane), PERBUTYL (registered trademark) O (t-butyl peroxy-2-ethylhexanoate), PERBUTYL (registered trademark) L (t-butyl peroxylaurate), PERBUTYL (registered trademark) I (t-butyl peroxy isopropyl monocarbonate), PERHEXYL (registered trademark) Z (t-hexyl peroxybenzoate), PERHEXA (registered trademark) 25Z (2,5-dimethyl-2,5-di(benzoylperoxy)hexane), and PERBUTYL (registered trademark) Z (t-butyl peroxybenzoate), all available from NOF Corporation.

In the polymerization of a monomer in the presence of the thermal polymerization initiator, the existence form of the thermal polymerization initiator is not particularly limited as long as the monomer is polymerized in conditions where the thermal polymerization initiator coexists with the monomer. Preferably, the thermal polymerization initiator is present as an adsorbate on the surface of rubber or a thermoplastic elastomer.

In an exemplary method for adsorbing the thermal polymerization initiator, e.g., an azo compound or a peroxide compound, to the surface of rubber or a thermoplastic elastomer, the surface portion of the rubber or thermoplastic elastomer to be modified is treated with a solution of the azo compound or peroxide compound dissolved in an organic solvent. This treatment allows the azo compound or peroxide compound to be adsorbed to the rubber or thermoplastic elastomer surface, so that thermal polymerization initiation points are formed, optionally after evaporating the organic solvent by drying. The surface may be treated by any method that allows the solution of the azo compound or peroxide compound to be brought into contact with the rubber or thermoplastic elastomer surface. Suitable examples include, for example, application or spraying of the azo or peroxide compound solution, and immersion into the solution. Moreover, if only part of the surface needs to be modified, it is sufficient to adsorb the thermal polymerization initiator only to the necessary part of the surface. In this case, for example, application or spraying of the solution is suitable.

Examples of the organic solvent include methanol, ethanol, acetone, benzene, toluene, methyl ethyl ketone, ethyl acetate, and tetrahydrofuran (THF). Preferred are aqueous organic solvents such as methanol, ethanol, or acetone because they are quickly dried or evaporated. More preferred are methanol, ethanol and acetone.

In an exemplary polymerization of a monomer in the presence of a thermal polymerization initiator, the thermal polymerization initiator adsorbed to the surface of rubber or a thermoplastic elastomer generates a radical by heat, and then the radical is transferred to the rubber or thermoplastic elastomer surface and, starting from this radical, a monomer is thermally polymerized. In particular, the monomer is preferably subjected to thermal radical polymerization by heating to 40° C. to 90° C. to grow polymer chains on the rubber or thermoplastic elastomer surface.

In exemplary methods for the polymerization of a monomer, a (liquid) monomer or a solution thereof is applied or coated (sprayed) onto the surface of rubber or a thermoplastic elastomer where a thermal polymerization initiator such as an azo compound or peroxide compound is present or adsorbed, or the rubber or thermoplastic elastomer is immersed in a (liquid) monomer or a solution thereof, followed by heating. This allows the radical polymerization (thermal radical polymerization) of the monomer to proceed so that polymer chains are grown on the rubber or thermoplastic elastomer surface. In another exemplary method, after the application, coating, spraying, or immersion, the rubber or thermoplastic elastomer surface may be covered with a transparent cover of glass, PET, polycarbonate, or the like and heated therethrough.

In addition to the above methods, the following exemplary methods for the polymerization of a monomer may be used: a thermal polymerization initiator such as an azo compound or peroxide compound and a monomer are mixed with water or an above-described organic solvent capable of dissolving the thermal polymerization initiator and a later-described solvent capable of dissolving the monomer to prepare a mixed solution, which is then applied or coated (sprayed) onto the surface of rubber or a thermoplastic elastomer, or rubber or a thermoplastic elastomer is immersed in the mixed solution, followed by heating.

The solvent for application (spraying), the method for application (spraying), the method for immersion, the conditions for heating, and the like may be conventionally known materials or methods. The solution of the monomer used is an aqueous solution of the monomer or a solution of the monomer dissolved in an organic solvent that hardly dissolves or does not dissolve the thermal polymerization initiator used (e.g., an azo compound). The (liquid) monomer or solution thereof used may contain a known polymerization inhibitor such as 4-methylphenol.

In the present invention, the radical polymerization of the monomer is allowed to proceed by heating after the application of the (liquid) monomer or a solution thereof or after the immersion into the (liquid) monomer or a solution thereof. The heating temperature and the time period of the polymerization may be appropriately chosen. Moreover, in order to prevent inhibition of the polymerization due to active gas such as oxygen in the reaction vessel, it is preferable to remove oxygen from the reaction vessel and the reaction solution during or before heating. To this end, appropriate operations may be performed. For example, an inert gas such as nitrogen gas or argon gas is inserted into the reaction vessel and the reaction solution to discharge active gas such as oxygen from the reaction system and replace the atmosphere in the reaction system with the inert gas. Oxygen may also be removed by vacuum deaeration.

The heating temperature for the polymerization of a monomer is preferably 40° C. to 90° C., more preferably 50° C. to 80° C. Heating at the above-mentioned temperature allows polymer chains to be formed well on the rubber or thermoplastic elastomer surface. In contrast, heating at lower than 40° C. may be insufficient to polymerize the monomer, while heating at higher than 90° C. may not allow for the use of the aqueous organic solvent and such heating in other organic solvents may increase the burden on the environment.

The heating time for the polymerization of a monomer is not particularly limited and may be appropriately chosen to allow the polymerization of a monomer to proceed sufficiently. In particular, the heating time is preferably 10 to 6000 minutes. The heating time within the above range allows polymer chains to be formed well on the rubber or thermoplastic elastomer surface. More preferably, the heating time is 30 minutes or longer, still more preferably 60 minutes or longer, while it is preferably 3000 minutes or shorter, more preferably 2500 minutes or shorter, particularly preferably 600 minutes or shorter.

The monomer to be polymerized in the presence of the thermal polymerization initiator is preferably at least one selected from the group consisting of a hydrophilic monomer, a metal salt-containing hydrophilic monomer, and a halogen-containing hydrophilic monomer. Examples of the hydrophilic monomer include hydrophilic monomers such as acrylic acid, acrylamide, and acrylonitrile, and ionic monomers having an ionic group in a substituent, a side chain or the like. Examples of the ionic monomer include monomers (cationic monomers) having a positive charge such as ammonium and phosphonium; and monomers (anionic monomers) having a negative charge such as a sulfonic acid group, a carboxyl group, a phosphoric acid group or a phosphonic acid group, or containing an acidic group that can be dissociated into a negatively charged group.

Specific examples of the ionic monomer include acrylic acid, methacrylic acid, itaconic acid, 3-vinylpropionic acid, vinylsulfonic acid, 2-sulfoethyl (meth)acrylate, 3-sulfopropyl (meth) acrylate, 2-acrylamide-2-methylpropanesulfonic acid, styrenesulfonic acid, and amine salts thereof; allylamine, 2-dimethylaminoethyl (meth)acrylate, and their hydrohalic acid salts; and 3-trimethylammonium propyl (meth) acrylate, 3-trimethylammonium propyl (meth) acrylamide, N,N,N-trimethyl-N-(hydroxy-3-methacryloyloxypropyl) ammonium chloride, and 2-(methacryloyloxy)ethyltrimethylammonium chloride (methacroylcholine chloride).

The hydrophilic monomer may suitably be a zwitterionic monomer (zwitterionic group-containing compound: compound bearing a center of permanent positive charge and a center of negative charge) such as a carboxybetaine, sulfobetaine, or phosphobetaine. The zwitterionic monomer may be a compound represented by Formula (1) below and especially suitably a compound represented by Formula (2) below, because then excellent sliding properties and excellent durability can be achieved.

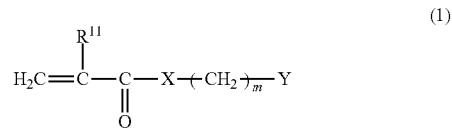

In Formula (1), $R^{11}$ represents —H or —$CH_3$; X represents —O— or —NH—; m represents an integer of 1 or more; and Y represents a zwitterionic group.

In Formula (1), preferably $R^{11}$ is —$CH_3$, X is —O—, and m is an integer of 1 to 10. In the zwitterionic group designated by Y, the cation may be a quaternary ammonium such as tetraalkylammonium, and the anion may be a carboxylic acid, sulfonic acid, phosphate or the like.

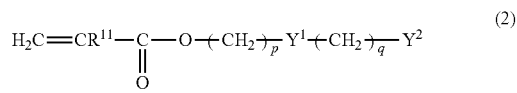

In Formula (2), $R^{11}$ represents —H or —$CH_3$; p and q each represent an integer of 1 or more; and $Y^1$ and $Y^2$ represent ionic functional groups having charges opposite to each other.

In Formula (2), p is preferably an integer of 2 or more, more preferably an integer of 2 to 10, and q is preferably an integer of 1 to 10, more preferably an integer of 2 to 4. Moreover, $R^{11}$ is preferably as defined above. $Y^1$ and $Y^2$ are as defined for the cation and anion above.

Typical suitable examples of the zwitterionic monomer include compounds represented by Formulae (2-1) to (2-4) below.

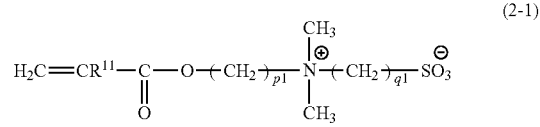

In Formula (2-1), $R^{11}$ represents a hydrogen atom or a methyl group, and p1 and q1 each represent an integer of 1 to 10.

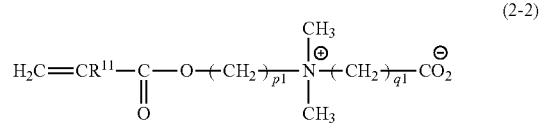

In Formula (2-2), $R^{11}$ represents a hydrogen atom or a methyl group, and p1 and q1 each represent an integer of 1 to 10.

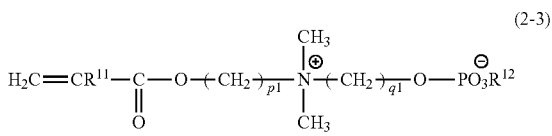
(2-3)

In Formula (2-3), $R^{11}$ represents a hydrogen atom or a methyl group, $R^{12}$ represents a C1-C6 hydrocarbon group, and p1 and q1 each represent an integer of 1 to 10.

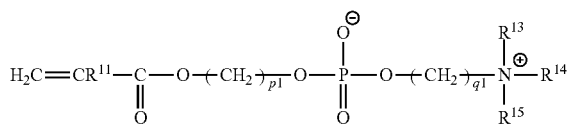
(2-4)

In Formula (2-4), $R^{11}$ represents a hydrogen atom or a methyl group; $R^{13}$, $R^{14}$, and $R^{15}$ are the same as or different from one another and each represent a C1 or C2 hydrocarbon group; and p1 and q1 each represent an integer of 1 to 10.

Examples of the compound represented by Formula (2-1) include dimethyl(3-sulfopropyl)(2-(meth)acryloyloxyethyl) ammonium betaine and [2-(methacryloyloxy)ethyl]dimethyl (3-sulfopropyl)aminium hydroxide. Examples of the compound represented by Formula (2-2) include dimethyl(2-carboxyethyl)-(2-(meth)acryloyloxyethyl) ammoniumbetaine. Examples of the compound represented by Formula (2-3) include dimethyl(3-methoxyphosphopropyl)-(2-(meth)acryloyloxyethyl)ammonium betaine. Examples of the compound represented by Formula (2-4) include 2-(meth)acryloyloxyethyl phosphorylcholine.

Examples of the metal salt-containing hydrophilic monomer include metal salts of acids such as acrylic acid, methacrylic acid, itaconic acid, 3-vinylpropionic acid, vinylsulfonic acid, 2-sulfoethyl (meth) acrylate, 3-sulfopropyl (meth) acrylate, 2-acrylamide-2-methylpropanesulfonic acid, and styrenesulfonic acid.

The metal salt is preferably an alkali metal salt, such as sodium or potassium, or an alkaline earth metal salt, such as calcium.

When the monomer used is a hydrophilic monomer containing a carboxylic acid such as acrylic acid or methacrylic acid, it may be converted to a metal salt using sodium hydroxide, potassium hydroxide, sodium hydrogen carbonate or the like after the polymerization reaction.

The halogen-containing hydrophilic monomer may be a monomer containing a hydrophilic group containing a halide salt such as chloride or bromide. Preferred are monomers containing a chloride-containing hydrophilic group and monomers containing a bromide-containing hydrophilic group. Preferred among these are compounds represented by Formula (3) below.

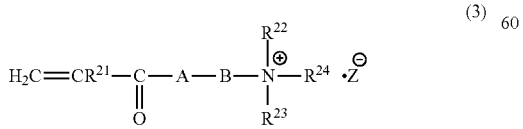
(3)

In Formula (3), A represents an oxygen atom or —NH—; B represents a C1-C4 alkylene group; $R^{21}$ represents a hydrogen atom or a methyl group; $R^{22}$, $R^{23}$, and $R^{24}$ are the same as or different from one another and each represent a C1-C4 alkyl group; and $Z^e$ represents a halogen ion.

In Formula (3), A is preferably an oxygen atom. Examples of B include linear or branched alkylene groups such as a methylene group, an ethylene group, and a propylene group, with a methylene group or an ethylene group being preferred. Examples of $R^{22}$, $R^{23}$, and $R^{24}$ include linear or branched alkyl groups such as a methyl group, an ethyl group, and a propyl group, with a methyl group or an ethyl group being preferred. Examples of Z (halogen atom) include fluorine, chlorine, and bromine. Among these, preferred is chlorine or bromine, and particularly preferred is chlorine.

Examples of the nitrogen-containing monomer represented by Formula (3) include 2-(methacryloyloxy)ethyltrimethylammonium chloride, 2-(acryloyloxy)ethyltrimethylammonium chloride, 2-(methacryloyloxy)ethyldimethylethylammonium chloride, and 2-(acryloyloxy)ethyldimethylethylammonium chloride.

In particular, the monomer is particularly preferably at least one selected from the group consisting of acrylic acid, acrylic acid metal salts, methacrylic acid, methacrylic acid metal salts, 3-sulfopropyl methacrylate potassium salt, 2-(methacryloyloxy)ethyltrimethylammonium chloride, 2-methacryloyloxyethyl phosphorylcholine, and [2-(methacryloyloxy)ethyl]dimethyl(3-sulfopropyl)aminium hydroxide as these monomers provide particularly excellent sliding properties and particularly excellent durability.

For excellent sliding properties and excellent durability, polymer chains represented by any of Formulae (4) to (7) below are preferably formed in the polymerization of a monomer. Such formed polymer chains also provide prevention of adsorption or aggregation of proteins.

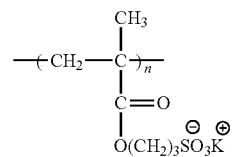
(4)

(n represents an integer of 1 or more.)

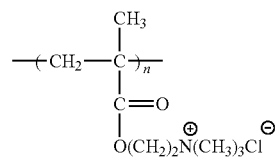
(5)

(n represents an integer of 1 or more.)

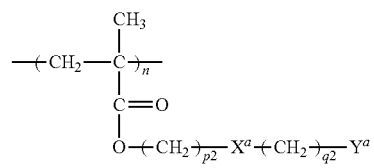
(6)

-continued

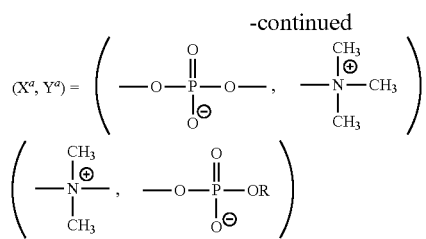

(n represents an integer of 1 or more; p2≥2; q2=2, 3, or 4; R represents a hydrocarbon group.)

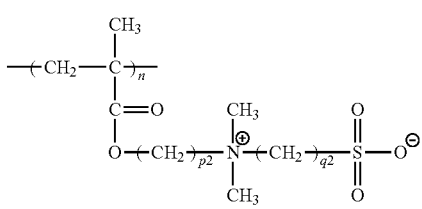

(n represents an integer of 1 or more; p2≥2; q2=2, 3, or 4)

In Formulae (4) to (7), n (polymerization degree) is preferably 20 to 5000, more preferably 200 to 2000. If n is less than 20, the polymer chains are so short that they may be concealed by irregularities on the rubber or thermoplastic elastomer surface, which tends to result in failure to provide sliding properties. If n is more than 5000, the amount of monomer used is increased, which tends to result in an economic disadvantage. Moreover, examples of the hydrocarbon group for R include a methyl group and an ethyl group.

The length of the formed polymer chain is preferably 10 to 5000 nm, more preferably 50 to 1000 nm. If the length is shorter than 10 nm, good sliding properties tend not to be achieved. If the length is longer than 5000 nm, a further improvement in sliding properties cannot be expected while the cost of starting materials tends to increase due to the use of the expensive monomer. In addition, surface patterns generated by the surface treatment tend to be visible to the naked eye and thereby spoil the appearance.

In the polymerization of a monomer, one kind of monomer or two or more kinds of monomers may be radically polymerized starting from the polymerization initiation points. Moreover, multiple kinds of polymer chains may be grown on the rubber or thermoplastic elastomer surface.

In the surface-modified rubbers or surface-modified thermoplastic elastomers of the present invention, the polymer chains formed by the polymerization of a monomer may be cross-linked to one another. In this case, the polymer chains may be cross-linked by ionic crosslinking, or crosslinking by a hydrophilic group containing an oxygen atom. Moreover, in the polymerization of a monomer, a small amount of a compound having at least two vinyl groups in a molecule may be added to introduce crosslinks between the polymer chains during the polymerization.

The compound having at least two vinyl groups in a molecule may suitably be N,N'-methylenebisacrylamide or the like.

Moreover, a preferred surface-modified rubber or surface-modified thermoplastic elastomer of the present invention is obtained by the polymerization of a monomer in the presence of a thermal polymerization initiator, followed by further treatment by polymerization of a monomer at least once in the presence of a thermal polymerization initiator optionally present as an adsorbate on the surface.

When the polymerization of a monomer in the presence of a thermal polymerization initiator is followed by further treatment by polymerization of a monomer at least once in the presence of a thermal polymerization initiator optionally present as an adsorbate on the surface, after the above-described polymerization of a monomer in the presence of a thermal polymerization initiator, polymerization of a monomer is performed again at least once in the presence of a thermal polymerization initiator optionally present as an adsorbate on the surface. This means that the treatment consisting of polymerization of a monomer in the presence of a thermal polymerization initiator is performed at least twice. As a result of such treatment, polymer layers are stacked on the rubber or thermoplastic elastomer surface, so that the sliding properties of the resulting surface-modified rubber or surface-modified thermoplastic elastomer can be further enhanced.

The method for polymerizing a monomer in the second and subsequent treatments is the same as that in the first treatment described above. When the treatment consisting of polymerization of a monomer in the presence of a thermal polymerization initiator is performed at least twice as mentioned above, it is preferable to perform, before the polymerization of a monomer in the (k+1)th treatment, treatment with a thermal polymerization initiator, and then polymerize a monomer in the (k+1)th treatment. After the polymerization of a monomer in the k-th treatment, polymerization of a monomer may be directly subsequently performed in the (k+1)th treatment. Or, after the polymerization of a monomer in the k-th treatment, unreacted monomers and the like may once be washed away from the surface of the resulting surface-modified rubber or surface-modified thermoplastic elastomer by washing with water, drying and the like, followed by polymerization of a monomer in the (k+1)th treatment. Here, the existence form of the thermal polymerization initiator used in the polymerization of a monomer in the (k+1) th treatment, the method for the treatment with the thermal polymerization initiator prior to the polymerization of a monomer in the (k+1)th treatment, and the kind of thermal polymerization initiator used are as described above.

It is to be noted that "k" in the present paragraph represents an integer of 1 or more.

Moreover, in the treatment method, the monomer used in the first treatment and the monomer used in the second or subsequent treatment may be the same as or different from each other. Furthermore, when the number of second and subsequent treatments is more than one, the monomers used in the plurality of treatments may be the same as or different from each other.

Particularly from the economical standpoint, when the treatment by polymerization of a monomer is performed n times (where n is an integer of 2 or more), it is more preferable to use in the first to (n−1)th treatments relatively inexpensive monomers such as acrylic acid, acrylamide, or acrylonitrile, and in the n-th treatment the aforementioned zwitterionic monomer such as 2-(meth)acryloyloxyethyl phosphorylcholine, or [2-(methacryloyloxy)ethyl]dimethyl (3-sulfopropyl)aminium hydroxide, the aforementioned metal salt-containing hydrophilic monomer such as a metal salt of an acid such as 3-sulfopropyl (meth)acrylate, or the aforementioned halogen-containing hydrophilic monomer such as 2-(methacryloyloxy)ethyltrimethylammonium chloride (methacroylcholine chloride) because then sliding properties are further improved even as compared to when, for example, the metal salt-containing hydrophilic monomer is used for n times.

Thus, in another suitable embodiment of the present invention, the surface-modified rubber or surface-modified thermoplastic elastomer is obtained by polymerization of at least one monomer selected from the group consisting of acrylic acid, acrylamide, and acrylonitrile in the presence of the thermal polymerization initiator, followed by further treatment by polymerization of at least one monomer selected from the group consisting of 2-(meth)acryloyloxyethyl phosphorylcholine, 3-sulfopropyl (meth)acrylate potassium salt, [2-(methacryloyloxy)ethyl]dimethyl(3-sulfopropyl)-aminium hydroxide, and methacroylcholine chloride at least once in the presence of a thermal polymerization initiator optionally present as an adsorbate on the surface.

As described above, the surface-modified rubbers or surface-modified thermoplastic elastomers of the present invention are obtainable by forming polymerization initiation points on the surface of rubber or a thermoplastic elastomer using a thermal polymerization initiator, and polymerizing a monomer starting from the polymerization initiation points to grow polymer chains on the rubber or thermoplastic elastomer surface.

Thus, the present invention also encompasses methods for modifying the surface of rubber or a thermoplastic elastomer, including the step of growing polymer chains on the surface of rubber or a thermoplastic elastomer by polymerizing a monomer in the presence of a thermal polymerization initiator on the surface of rubber or a thermoplastic elastomer.

In the above step, first, polymerization initiation points are formed on the surface of rubber or a thermoplastic elastomer. This can be accomplished, for example, by adsorbing the thermal polymerization initiator to the rubber or thermoplastic elastomer surface to form polymerization initiation points.

The thermal polymerization initiator is as described above. The method for adsorbing the thermal polymerization initiator to the rubber or thermoplastic elastomer surface and the method for heating are also as described above.

In the above step, a monomer is polymerized (radically polymerized) starting from the polymerization initiation points to grow polymer chains on the surface of rubber or a thermoplastic elastomer. The kind of monomer and the polymerization method are as described above.

Moreover, the methods for modifying the surface of rubber or a thermoplastic elastomer may include, after the step of growing polymer chains, the step of further polymerizing a monomer at least once in the presence of a thermal polymerization initiator optionally present as an adsorbate on the surface. Repeating at least twice the step of polymerizing a monomer in the presence of a thermal polymerization initiator as described above allows the surface-modified rubber or surface-modified thermoplastic elastomer to have more improved sliding properties. The method for repeating at least twice the treatment of polymerizing a monomer in the presence of a thermal polymerization initiator, the kind of monomer used, the existence form of the thermal polymerization initiator, the method for the treatment with the thermal polymerization initiator, the kind of thermal polymerization initiator used, and the like are as described above.

Exemplary materials of the surface-modified rubbers or surface-modified thermoplastic elastomers of the present invention include natural rubber, deproteinized natural rubber, silicone rubber, nylon, and polyurethane. Preferred among these are deproteinized natural rubber, nylon, and polyurethane in view of bonding between the rubber or thermoplastic elastomer surface and the lubricant layer and biocompatibility. Thus, in another suitable embodiment of the present invention, the surface-modified rubber or surface-modified thermoplastic elastomer of the present invention includes at least one selected from the group consisting of natural rubber, deproteinized natural rubber, silicone rubber, nylon, and polyurethane, and particularly preferably from the group consisting of deproteinized natural rubber, nylon, and polyurethane.

In the surface-modified rubbers or surface-modified thermoplastic elastomers of the present invention, the rubber or thermoplastic elastomer surface is imparted with lubricity and, further, the durability of the lubricant layer on the surface is improved so that deterioration of the sliding properties of the rubber or thermoplastic elastomer can be suppressed. Such surface-modified rubbers or surface-modified thermoplastic elastomers can be suitably used for example for medical devices, e.g., catheters, syringe barrels, and tubes of medical instruments such as medical devices or equipment. Thus, the present invention also encompasses medical devices including the surface-modified rubber or surface-modified thermoplastic elastomer. In another suitable embodiment of the present invention, the medical device is a catheter, a syringe barrel, or a tube of a medical instrument.

Moreover, by applying the modification method to at least part of a three-dimensional rubber or thermoplastic elastomer, a surface-modified three-dimensional rubber or thermoplastic elastomer can be obtained. Further, preferred examples of such a modified rubber or thermoplastic elastomer surface include polymer brushes. The polymer brush as used herein refers to an assembly of graft polymer molecules obtained in the "grafting from" approach by surface-initiated living radical polymerization. Moreover, the graft chains are preferably oriented in a direction substantially vertical to the rubber or thermoplastic elastomer surface because then the entropy is reduced and thus the molecular mobility of the graft chains is reduced so that sliding properties are provided. Furthermore, semidilute or concentrated brushes having a brush density of 0.01 chains/$nm^2$ or higher are preferred.

EXAMPLES

The present invention is more specifically described by reference to examples below but is not limited only to these examples.

Example 1

The surface of a nylon flat plate (1 cm×2 cm, 1 mm in thickness) was washed with acetone and then dried.

The washed nylon plate was placed in a glass vessel containing 0.02 M azobisisobutyronitrile (AIBN) and 1.2 M 3-sulfopropyl methacrylate potassium salt in a water/ethanol (1:1) mixed solution, and the glass vessel was covered with a lid.

After the glass vessel was purged with argon, it was heated in a 60° C. water bath for 5 hours to cause surface-initiated radical polymerization. Subsequently, the surface was washed with water to wash away unreacted monomers and the like. In this manner, a surface-modified thermoplastic elastomer was prepared. The surface-modified thermoplastic elastomer was evaluated for sliding properties as described later.

Example 2

A surface-modified thermoplastic elastomer was prepared by carrying out surface-initiated radical polymerization in the same manner as in Example 1, except that the nylon flat plate was changed to a nylon tube. The surface-modified thermoplastic elastomer was evaluated for sliding properties as described later.

Example 3

A surface-modified thermoplastic elastomer was prepared by carrying out surface-initiated radical polymerization in the same manner as in Example 1, except that the nylon flat plate was changed to a polyurethane flat plate. The surface-modified thermoplastic elastomer was evaluated for sliding properties as described later.

Example 4

A surface-modified thermoplastic elastomer was prepared by carrying out surface-initiated radical polymerization in the same manner as in Example 1, except that 3-sulfopropyl methacrylate potassium salt was changed to 2-(methacryloyloxy) ethyltrimethylammonium chloride. The surface-modified thermoplastic elastomer was evaluated for sliding properties as described later.

Example 5

A surface-modified thermoplastic elastomer was prepared by carrying out surface-initiated radical polymerization in the same manner as in Example 1, except that 3-sulfopropyl methacrylate potassium salt was changed to 2-methacryloyloxyethyl phosphorylcholine. The surface-modified thermoplastic elastomer was evaluated for sliding properties as described later.

Example 6

A surface-modified thermoplastic elastomer was prepared by carrying out surface-initiated radical polymerization in the same manner as in Example 1, except that 3-sulfopropyl methacrylate potassium salt was changed to [2-(methacryloyloxy)ethyl]dimethyl(3-sulfopropyl)aminium hydroxide. The surface-modified thermoplastic elastomer was evaluated for sliding properties as described later.

Example 7

A surface-modified rubber was prepared by carrying out surface-initiated radical polymerization in the same manner as in Example 1, except that the nylon flat plate was changed to a flat plate of vulcanized deproteinized natural rubber. The surface-modified rubber was evaluated for sliding properties as described later.

Example 8

The surface of a nylon flat plate (1 cm×2 cm, 1 mm in thickness) was washed with acetone and then dried.

The washed nylon plate was immersed in a 1.5% by mass solution of azobisisobutyronitrile (AIBN) in ethanol for 5 minutes, and then taken out and dried.

The resulting nylon plate was placed in a glass vessel containing a 1.2 M aqueous solution of 3-sulfopropyl methacrylate potassium salt, and the glass vessel was covered with a lid.

After the glass vessel was purged with argon, it was heated in a 60° C. water bath for 5 hours to cause surface-initiated radical polymerization. Subsequently, the surface was washed with water to wash away unreacted monomers and the like. In this manner, a surface-modified thermoplastic elastomer was prepared. The surface-modified thermoplastic elastomer was evaluated for sliding properties as described later.

Example 9

A surface-modified thermoplastic elastomer was prepared by carrying out surface-initiated radical polymerization in the same manner as in Example 8, except that 3-sulfopropyl methacrylate potassium salt was changed to 2-(methacryloyloxy)ethyltrimethylammonium chloride. The surface-modified thermoplastic elastomer was evaluated for sliding properties as described later.

Example 10

The surface of a nylon flat plate (1 cm×2 cm, 1 mm in thickness) was washed with acetone and then dried.

The washed nylon plate was immersed in a 1.5% by mass solution of azobisisobutyronitrile (AIBN) in ethanol for 5 minutes, and then taken out and dried. The resulting nylon plate was placed in a glass vessel containing a 1.2 M acrylic acid aqueous solution, and the glass vessel was covered with a lid.

After the glass vessel was purged with argon, it was heated in a 60° C. water bath for 3 hours to cause surface-initiated radical polymerization. Subsequently, the surface was washed with water to wash away unreacted monomers and the like.

Next, the washed nylon plate was immersed again in a 1.5% by mass solution of azobisisobutyronitrile (AIBN) in ethanol for 5 minutes, and then taken out and dried. The resulting nylon plate was placed in a glass vessel containing a 1.2 M aqueous solution of 3-sulfopropyl methacrylate potassium salt, and the glass vessel was covered with a lid.

After the glass vessel was purged with argon, it was heated in a 60° C. water bath for 5 hours to cause surface-initiated radical polymerization. Subsequently, the surface was washed with water to wash away unreacted monomers and the like. In this manner, a surface-modified thermoplastic elastomer was prepared. The surface-modified thermoplastic elastomer was evaluated for sliding properties as described later.

Example 11

A surface-modified thermoplastic elastomer was prepared by carrying out surface-initiated radical polymerization in the same manner as in Example 10, except that 3-sulfopropyl methacrylate potassium salt was changed to 2-(methacryloyloxy)ethyltrimethylammonium chloride. The surface-modified thermoplastic elastomer was evaluated for sliding properties as described later.

Example 12

The surface of a nylon flat plate (1 cm×2 cm, 1 mm in thickness) was washed with acetone and then dried.

The washed nylon plate was placed in a glass vessel containing 0.02 M azobisisobutyronitrile (AIBN) and 1.2 M acrylic acid in a water/ethanol (1:1) mixed solution, and the glass vessel was covered with a lid.

After the glass vessel was purged with argon, it was heated in a 60° C. water bath for 3 hours to cause surface-initiated radical polymerization. Subsequently, the surface was washed with water to wash away unreacted monomers and the like.

Next, the washed nylon plate was placed in a glass vessel containing 0.02 M azobisisobutyronitrile (AIBN) and 1.2 M 3-sulfopropyl methacrylate potassium salt in a water/ethanol (1:1) mixed solution, and the glass vessel was covered with a lid.

After the glass vessel was purged with argon, it was heated in a 60° C. water bath for 5 hours to cause surface-initiated radical polymerization. Subsequently, the surface was washed with water to wash away unreacted monomers and the like. In this manner, a surface-modified thermoplastic elastomer was prepared. The surface-modified thermoplastic elastomer was evaluated for sliding properties as described later.

Comparative Example 1

The surface of a nylon flat plate (1 cm×2 cm, 1 mm in thickness) washed with acetone and then dried was evaluated for sliding properties as described later.

Comparative Example 2

A nylon tube only washed with acetone and then dried was evaluated for sliding properties as described later.

Comparative Example 3

The surface of a nylon flat plate (1 cm×2 cm, 1 mm in thickness) was washed with acetone and then dried. A maleic anhydride-based polymer, which is a common lubricant, was applied to the surface of the dried nylon plate to prepare a comparative surface-modified thermoplastic elastomer. The comparative surface-modified thermoplastic elastomer was evaluated for sliding properties as described later.

Evaluation of Sliding Properties

Each surface-modified rubber, surface-modified thermoplastic elastomer, comparative surface-modified thermoplastic elastomer, flat plate, or tube was watered and rubbed by a hand to evaluate sliding properties.

As a result of the evaluation, the surfaces of Comparative Examples 1 and 2 were found not to be slippery but to have a feel like the original thermoplastic elastomer (nylon) surface and thus low sliding properties. When compared to these surfaces, the surfaces of Comparative Example 3 and Examples 1 to 12 were slippery and had significantly improved sliding properties. Particularly, the surfaces of Examples 10 to 12 were more slippery and had more improved sliding properties than the surface of Example 1.

Moreover, the surfaces of Examples 1 to 12 remained slippery and showed no change in sliding properties after rubbing 500 times by a hand. The surface of Comparative Example 3 had similar sliding properties to the initial sliding properties until it was rubbed 200 times by a hand. Thereafter, however, the sliding properties of Comparative Example 3 gradually deteriorated, reaching similar sliding properties to that of Comparative Example 1 after rubbing 500 times.

The invention claimed is:

1. A method for modifying a surface of rubber or a thermoplastic elastomer, comprising the step of growing polymer chains on the surface of rubber or a thermoplastic elastomer by polymerizing a monomer in the presence of a thermal polymerization initiator on the surface of the rubber or the thermoplastic elastomer,
wherein
the rubber or the thermoplastic elastomer is natural rubber, deproteinized natural rubber, nylon, or polyurethane;
the monomer is at least one selected from the group consisting of
[2-(methacryloyloxy)ethyl]dimethyl(3-sulfopropyl) aminium hydroxide;
a metal salt of itaconic acid, 3-vinylpropionic acid, vinylsulfonic acid, 2-sulfoethyl (meth)acrylate, 3-sulfopropyl (meth)acrylate, 2-acrylamide-2-methylpropanesulfonic acid, or styrenesulfonic acid;
a monomer containing a chloride-containing hydrophilic group; and
a monomer containing a bromide-containing hydrophilic group; and
the thermal polymerization initiator is azobisisobutyronitrile.

2. The method for modifying a surface of rubber or a thermoplastic elastomer according to claim 1, comprising, after the step of growing polymer chains, the step of further polymerizing a monomer at least once in the presence of a thermal polymerization initiator optionally present as an adsorbate on the surface.

3. The method for modifying a surface of rubber or a thermoplastic elastomer according to claim 1, comprising, after the step of growing polymer chains, the step of further polymerizing a monomer at least once in the presence of a thermal polymerization initiator present as an adsorbate on the surface.

4. The method for modifying a surface of rubber or a thermoplastic elastomer according to claim 1,
the monomer is at least one selected from the group consisting of 3-sulfopropyl methacrylate potassium salt, 2-(methacryloyloxy)ethyltrimethylammonium chloride, and [2-(methacryloyloxy)ethyl]dimethyl(3-sulfopropyl)aminium hydroxide.

* * * * *